United States Patent [19]

Lam et al.

[11] Patent Number: 5,814,096
[45] Date of Patent: Sep. 29, 1998

[54] SIZING OBTURATOR FOR PROSTHETIC AORTIC VALVES

[75] Inventors: Hung Lam, Norco; Lisa Deseran, Manhattan Beach; Richard Rhee, Diamond Bar, all of Calif.

[73] Assignee: Baxter International Inc., Deerfield, Ill.

[21] Appl. No.: 960,083

[22] Filed: Oct. 24, 1997

Related U.S. Application Data

[63] Continuation of Ser. No. 583,811, Jan. 5, 1996, abandoned.

[51] Int. Cl.$^6$ .................................................... A61F 2/24
[52] U.S. Cl. ............................................. 623/2; 128/774
[58] Field of Search ................................ 623/2, 66, 900; 128/774; 606/1

[56] References Cited

U.S. PATENT DOCUMENTS

| | | | |
|---|---|---|---|
| 4,441,216 | 4/1984 | Ionescu et al. | 623/2 |
| 4,626,255 | 12/1986 | Reichart et al. | 623/2 |
| 5,042,161 | 8/1991 | Hodge | 128/174 |
| 5,360,014 | 11/1994 | Sauter et al. | 623/2 |
| 5,489,296 | 2/1996 | Love et al. | 128/774 |
| 5,531,785 | 7/1996 | Love et al. | 623/900 |

FOREIGN PATENT DOCUMENTS

| | | |
|---|---|---|
| 2 418 918 | 9/1979 | France . |
| 2 083 362 | 3/1982 | United Kingdom . |

OTHER PUBLICATIONS

Booklet entitled "Carpentier–Edwards® pericardial Bioprostheses Mini–Synmposium", Chicago, Illinois, Baxter Healthcare Corporation, Edwards CVS Division, Apr. 24, 1993.

Technique fpr Aortic Valve Replacement With the Carpentier–Edwards® Porcine Aortic Valve Bioprosthesis, Baxter Healthcare Corporation, Edwards CVS Division, 1991.

Brochure entitled "Judge Our Pericardial Valve by its Appearance and You Will Only Get Half the Picture", Edwards CVS Division, Baxter Healthcare Corporation, 1994.

Brochure entitled "Judge Our Pericardial Valve by its Appearance and You Will Only Get Half the Picture", Edwards CVS Division, Baxter Healthcare Corporation, 1989.

*Primary Examiner*—Robert A. Clarke
*Assistant Examiner*—Bruce E. Snow
*Attorney, Agent, or Firm*—Guy L. Cumberbach; Robert D. Buyan

[57] ABSTRACT

An aortic valve sizing obturator apparatus for employment in determining the correct size of an aortic annulus. The apparatus includes a cylindrical obturator body with a flange member formed thereabout. At least the under surface of the flange member is of a non-planar, multi-curvate configuration to thereby be complimentary in shape to the annulus of an aortic valve when seated in the annulus during size determination. Within the cylindrical obturator body can be disposed a handle connector to which a handle can be attached during placement of the obturator apparatus within an annulus. The present invention also includes methodology for determining the size of an aortic valve annulus by employing a plurality of differently-sized aortic valve sizing obturators defined above and individually seating them sequentially within the aortic annulus until an obturator that reflects annulus size is located.

31 Claims, 3 Drawing Sheets

SIZING OBTURATOR FOR PROSTHETIC AORTIC VALVES

This application is a continuation of U.S. application Ser. No. 08/583,811 filed Jan. 5, 1996, now abandoned.

FIELD OF THE INVENTION

The present invention pertains generally to medical devices and more particularly to an obturator apparatus insertable into an aortic valve annulus of a human heart following performance of a valvulotomy for the purpose of determining the correct size of a prosthetic valve to be surgically implanted therein.

BACKGROUND OF THE INVENTION

Surgical valvulotomy and prosthetic valve replacement has been performed in human beings for many years. Most frequently, the procedures are utilized to replace mitral or aortic valves in patients who suffer from valvular heart disease.

In particular, surgical replacement of the aortic valve is typically necessitated by a) obstruction (i.e., stenosis) of the aortic heart valve or b) leakage (i.e., regurgitation, incompetence or insufficiency) of blood through the aortic valve. In some patients, symptoms of both obstruction and leakage are present, this being known as "mixed disease" or "combined lesions". Aortic valvular heart disease may be caused by a number of factors, including congenital deformations, infections, degenerative calcification, and certain rheumatological heart disorders.

Surgical replacement of the aortic valve is typically performed under general anesthesia, with full cardiopulmonary bypass. The leaflets of the endogenous aortic valve are removed along with any calcified surrounding tissue. This results in the formation of an annular opening at the site of the endogenous aortic valve. Thereafter, a mechanical or bioprosthetic aortic valve is then selected and sutured into the annular valve opening, as a prosthetic replacement for the surgically-removed endogenous valve. Examples of mechanical prosthetic aortic valves which have heretofore been utilized, include the Starr-Edwards™ Silastic Ball Valve (Baxter Healthcare Corporation, Edwards CVC Division, 17221 Red Hill Ave., P.O. Box 11150, Santa Ana, Calif. 92711-1150); the St. Jude Bileaflet Heart Valve (St. Jude Medical, Inc., St. Paul, Minn.) and the Medtronic-Hall Tilting Disk Valve (Medtronic Inc., Minneapolis, Minn.). Examples of bioprosthetic aortic valves which have heretofore been utilized include the Carpentier-Edwards®, PERIMOUNT™ Pericardial Bioprosthesis (Baxter Healthcare Corporation, Edwards CVS Division, 17221 Red Hill Ave., P.O. Box 11150, Santa Ana, Calif. 92711-1150) as well as the Carpentier-Edwards® Porcine Bioprosthesis (Baxter Healthcare Corporation, Edwards CVC Division, 17221 Red Hill Ave., P.O. Box 11150, Santa Ana, Calif. 92711-1150).

In general, these prosthetic aortic valves comprise a cylindrical valve body having a blood flow passageway extending longitudinally therethrough, and a suture ring formed annularly thereabout. The suture ring comprises suture penetrable material or a series of suture passage apertures, to facilitate anastomosis of the suture ring to the adjacent surgically-prepared aortic annulus. Because of the tricuspid configuration of the endogenous aortic valve, the natural aortic root has a non-planar, multi-curvate configuration. To correspond to such anatomical configuration of the natural aortic root, some or all of the aortic prosthetic valve of the prior art have utilized suture rings which are of a generally non-planar, multi-curvate configuration.

The ultimate success of any aortic valve placement procedure is dependant on a number of factors, including the correct sizing and placement of the prosthetic aortic valve. In this regard, it is common practice to utilize a sizing obturator to determine the correct size of prosthetic valve for implantation. Such sizing obturators typically comprise a series of different-sized cylindrical members which are independently attachable to a handle, and which are insertable into the surgically-prepared valve annulus to determine the actual size of the annular opening. Such sizing obturators may be color-coded for size identification. Examples of aortic and mitral valve sizing obturators of the prior art include the True-Size™ Aortic Obturator-Model 1161 and the True-Size™ Mitral Obturator-Model 1162, Baxter Healthcare Corporation, Edwards CVS Division, 17221 Red Hill Ave., P.O. Box 1150, Santa Ana, Calif. 92711-1150.

One drawback associated with aortic valve sizing obturators of the prior art is that such obturators typically comprise a generally cylindrical obturator body having a flat annular flange extending therearound. The flat annular flange is typically advanced into abutment with, but does not actually seat or nest within, the non-planar, three-peaked anatomy of the natural aortic root, which defines the superior aspect of the aortic annulus.

SUMMARY OF THE INVENTION

In view of the importance of ascertaining the correct size and configuration of the prosthetic aortic valve to be utilized, there exists a need in the art for the development of a new sizing obturator device which has a non-planar, multi-curvate flange configured to directly seat or nest within the three-peaked normal anatomy of the superior aspect of the annular, thereby providing the surgeon with an accurate, preliminary reading of the correct size and configuration of non-planar, multi-curvate suture ring to be utilized.

Accordingly, a primary object of the present invention is to provide a sizing obturator which has a cylindrical body which may be inserted through the annulus, and a flange member which is configured to be substantially complimentary to the configuration of the superior aspect of the aortic annulus, within which a prosthetic valve is to be subsequently implanted.

Another object of the present invention is to provide such a sizing obturator whose cylindrical body has, disposed therein, a connector member which is connectable to a handle usable during obturator placement.

Yet another object of the present invention is to provide methodology employing the above-defined obturator in a plurality of sizes to thereby accurately reflect aortic annulus size for subsequent prosthetic valve implantation.

These and other objects of the present invention will become apparent throughout the description of the invention which now follows.

The present invention is an aortic valve sizing obturator apparatus for employment in determining the correct size of an aortic annulus so that a correctly sized prosthetic valve can be chosen for subsequent placement within the annulus. The apparatus comprises a cylindrical obturator body having a top end, a bottom end, an inner surface, an outer surface, and a first outer diameter. A flange member is formed about the obturator body and has an upper surface, an under surface, and a second outer diameter which is greater than the first outer diameter of the obturator body. The undersurface of the flange member is of a non-planar, multi-curvate (i.e., having more than one curve formed therein) configuration to thereby be complimentary in shape to the superior aspect of the aortic annulus such that the flange may be seated or nested within the supra-annular anatomy (three peaked configuration of the aortic root during size determination. Within the cylindrical obturator body, there may be disposed a handle connector apparatus, to which a separate handle can be attached to facilitate insertion and placement of the obturator apparatus during the sizing procedure.

The present invention also includes methodology for determining the size of an aortic valve annulus for subsequent placement therein of a prosthetic aortic valve. This methodology employs a plurality of aortic valve sizing obturators defined above and includes placing of one or more obturators, one at a time, into an aortic valve annulus such that the flange member is seated in a complimentary relationship with the configuration of the annulus. This procedure continues until a properly sized obturator that reflects the size of the aortic annulus, is located.

By employing the present invention in a procedure wherein a prosthetic aortic valve is to be implanted, a surgeon is able to accurately determine the size needed for the replacement valve. Achieving such accuracy is greatly enhanced because of the non-planar, multi-curvate flange member described above which permits seating of the flange in a complimentary relationship with the configuration of the aortic annulus to thereby gain a more accurate reflection of the size of the annulus and of the consequent replacement valve.

DETAILED DESCRIPTION OF THE PREFERRED EMBODIMENT

Figure 1:
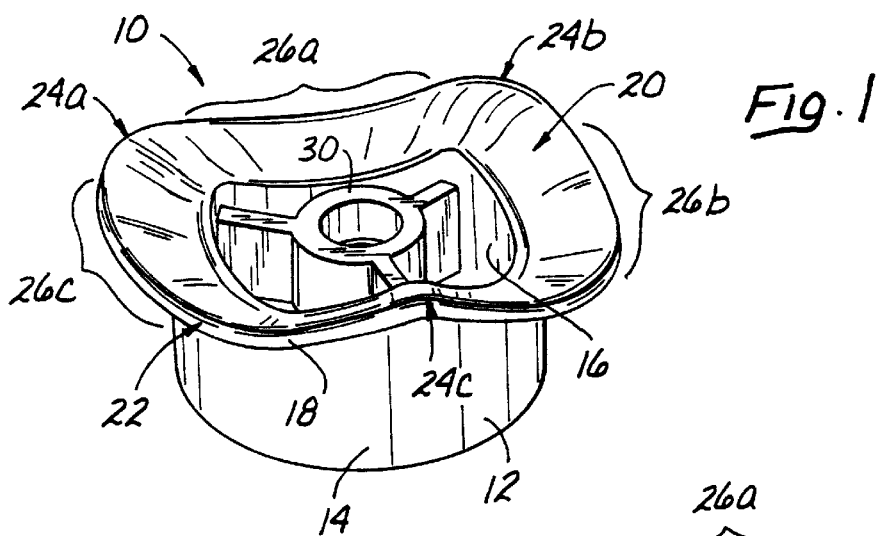
FIG. 1 is top perspective view of a preferred aortic valve sizing obturator of the present invention.
Figure 2:
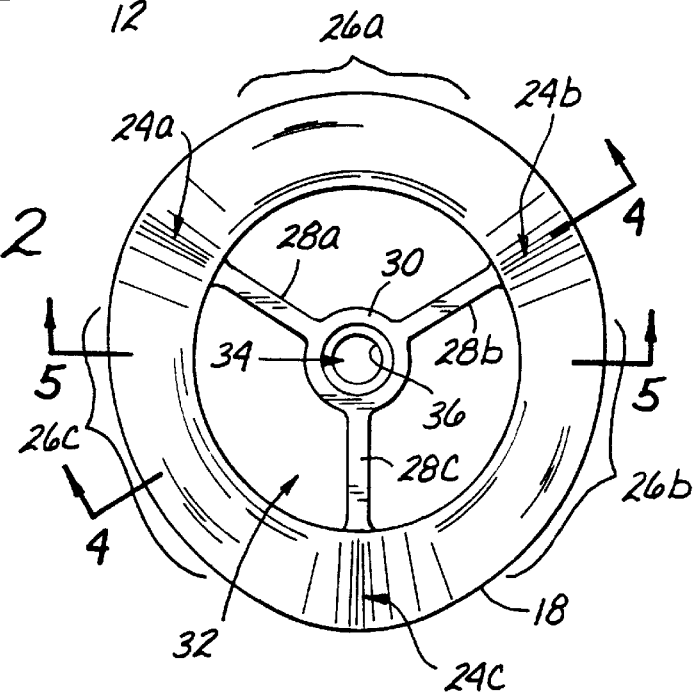
FIG. 2 is a top plan view of the preferred aortic valve sizing obturator of FIG. 1.

The following detailed description and the accompanying drawings are provided for the purpose of describing and illustrating a presently preferred embodiment of the invention only, and are not intended to limit the scope of the invention in any way.

With reference to the drawings, the preferred aortic valve sizing obturator 10 of the present invention comprises a cylindrical obturator body 12 having an outer surface 14 and an inner surface 16, and a non-planar, multi-curvate annular flange 18 extending outwardly about one end of the cylindrical obturator body 12. The non-planar, multi-curvate annular flange 18 has an upper surface 20, and a lower surface 22. (As used in this patent application, the term "multi-curvate" means having more than one curve formed therein.)

The end of the cylindrical obturator body 12 upon which the non-planar, multi-curvate flange 18 is positioned, and the configuration of the non-planar, multi-curvate flange 18 itself, are characterized by the presence of three equally-spaced-apart blunt peaks 24a, 24b, 24c having three generally arcuate depressions 26a, 26b, 26c extending therebetween, as shown.

Three (3) radial strut members 28a, 28b, 28c extend inwardly from the inner surface 16 of the cylindrical obturator body 12 at locations which are immediately below each of the discrete blunt peaks 24a, 24b, 24c formed in the non-planar, multi-curvate flange 18. A cylindrical inner member 30 is positioned coaxially within the central bore 32 of the cylindrical obturator body 12, and is supported and held in fixed position by the strut members 28a, 28b, 28c. A hollow inner bore 34 extends longitudinally through the inner cylindrical member 30, and internal threads 36 are formed on the inner surface of such longitudinal bore 34.

Figure 4:
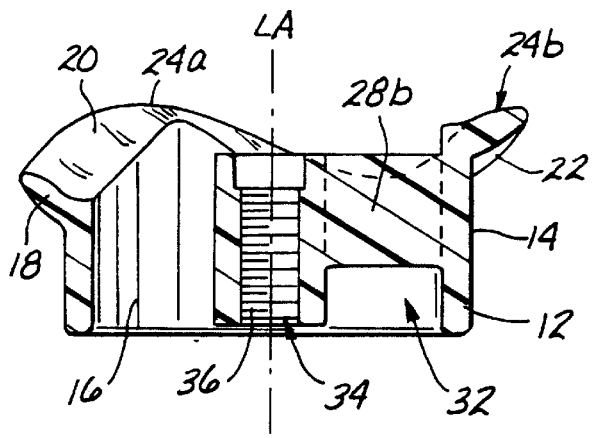
FIG. 4 is a cross sectional view through line 4—4 of FIG. 2.
Figure 3:
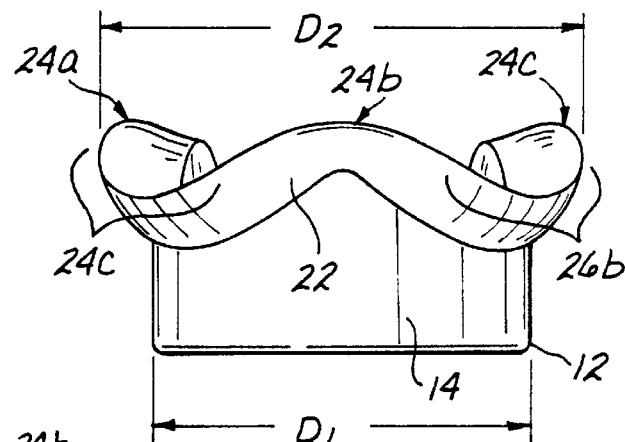
FIG. 3 is a side elevational view of the preferred aortic valve sizing obturator of FIG. 1.
Figure 5:
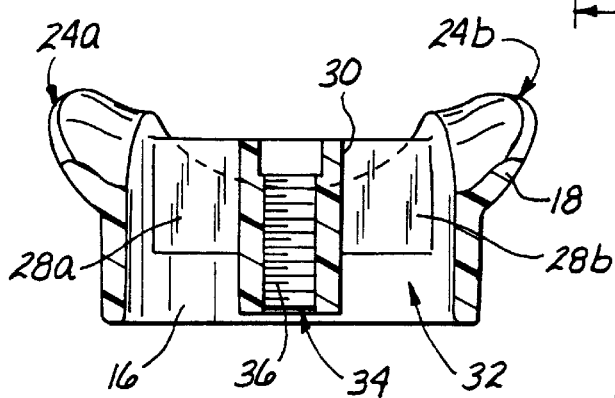
FIG. 5 is a cross sectional view through line 5—5 of FIG. 2.

A single longitudinal axis LA as illustrated in FIG. 4 is projectable longitudinally through the cylindrical obturator body 12, such that the obturator body 12 and inner cylindrical member 30 are coaxially disposed about such common longitudinal axis LA.

Figure 6A:
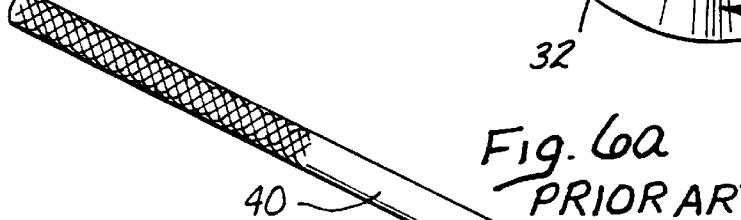
FIG. 6a is a perspective view of a prior art handle member which may be utilized in conjunction with the preferred aortic valve sizing obturator of the present invention.
Figure 6B:
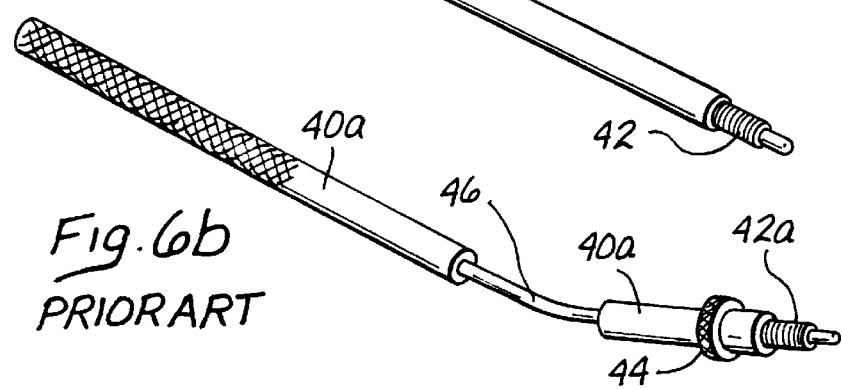
FIG. 6b is a perspective view of an alternative, bendable, handle member which may be utilized in conjunction with the aortic valve sizing obturator of the present invention.

FIG. 6a–6b show two prior art stainless steel handles which may be utilized in conjunction with the preferred aortic valve sizing obturator shown in FIGS. 1–5. Specifically, FIG. 6a shows a reusable handle comprising an elongate rigid handle member 40 having an externally threaded distal projection 42 extending from the distal end thereof. The externally threaded projection 42 is insertable into the upper end of the bore 34 of the inner cylindrical member 30 of the preferred aortic valve sizing obturator 10 of the present invention such that the external threads of projection 42 may be rotatably engaged with the internal threads 36 formed within the bore 34 of the inner cylindrical member 30, thereby attaching the elongate handle member 40 to the aortic valve sizing obturator 10. The particular handle shown in FIG. 6a has been commercially available as Handle Model 1108, Baxter Healthcare Corporation, Edwards CVC Division, 17221 Red Hill Ave., P.O. Box 11150, Santa Ana, Calif. 92711-1150.

FIG. 6b shows an alternative handle which comprises a segmented rigid handle member 40a having a bendable segment 46 disposed therewithin, and an externally threaded distal projection 42a extending from the distal end thereof. A flanged bushing 44 is formed proximal to the externally threaded distal portion 42a, as shown. The bendable segment 46 of this handle may be manually bent or preformed by the surgeon to a desired configuration to facilitate insertion and positioning of the aortic valve sizing obturator 10. The particular handle shown in FIG. 6b has been commercially available as Handle Model 1111, Baxter Healthcare Corporation Edwards CVC Division, 17221 Red Hill Ave., P.O. Box 11150, Santa Ana, Calif. 92711-1150.

The aortic valve sizing obturator 10 may be formed of any suitable material including rigid, autoclavable thermoplastic material such as polysulfonate. The obturators 10 will typically be provided in a kit consisting of a series of different-sized obturators 10, corresponding to the available sizes of the particular prosthetic heart valves for which the obturator 10 is to be employed. For example, the following table shows examples of specific component dimensions (in millimeters) of standard, commercially available sizes of the Carpentier-Edwards® PERIMOUNT™ Pericardial Aortic Bioprosthesis referred to hereabove:

| Mounting Diameter (Annulus) | 19 | 21 | 23 | 25 | 27 | 29 |
|---|---|---|---|---|---|---|
| Internal Diameter (Stent I.D.) | 18 | 20 | 22 | 24 | 26 | 28 |
| Profile Height | 13 | 14 | 15 | 16 | 17 | 18 |
| External Sewing Ring Diameter | 28 | 31 | 33 | 35 | 38 | 40 |

When the sizing obturator 10 of the present invention is to be used for determining the correct size of the Model 2700 Aortic Bioprosthesis to be employed, the manufacturer will typically provide a kit having a series of different-sized obturators 10, which correspond directly to the available sizes of the Model 2700 Aortic Valvular Prosthesis. In this regard, if an obturator 10 having a mounting diameter (i.e., the diameter of the outer surface 14 of the cylindrical obturator body 12) of 19 is found to provide the best fit within the surgically-prepared valve annulus, a Model 2700 prosthetic valve having a mounting diameter of 19 will typically be selected. Also, because the sizing obturator 10 of the present invention is provided with a non-planar, multi-curvate flange 18, such flange may be directly nested or seated within the surgically-prepared natural valve annulus to provide a direct and precise indication of the correct external sewing ring diameter desired.

It will be appreciated that, in most aortic valve replacement surgeries, the prosthetic valve is implanted in a supra-annular position wherein the suture ring of the prosthetic valve is positioned superior to the surgically-prepared valve annulus. Alternatively, however, it may sometimes be desirable to implant the prosthetic valve in an intra-annular position, wherein the entire suture ring of the prosthetic valve is positioned within the surgically-prepared valve annulus and an everting mattress suture technique is employed to anastomose the prosthetic valve in such intra-annular position. In this regard, when it is desired to utilize the typical supra-annular positioning of the prosthetic valve, the sizing obturator 10 will be inserted such that the non-planar, multi-curvate flange 18 is nested or seated in a supra-annular position which is analogous to the intended positioning of the suturing ring of the prosthetic valve. Alternatively, however, if it is intended to implant the prosthetic valve in an intra-annular position, the sizing obturator 10 of the present invention will be initially placed such that the non-planar, multi-curvate annular flange 18 is located in the desired intra-annular position.

Figure 7A:
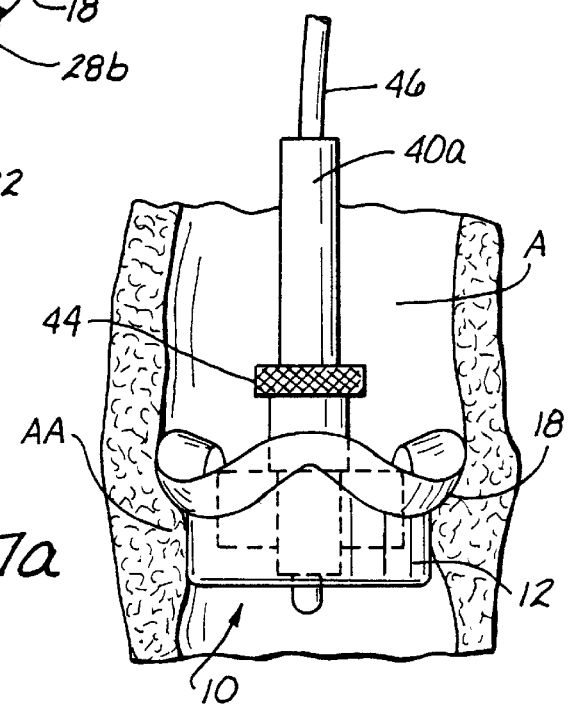
FIG. 7a is an enlarged elevational view of a portion of FIG. 7.
Figure 7:
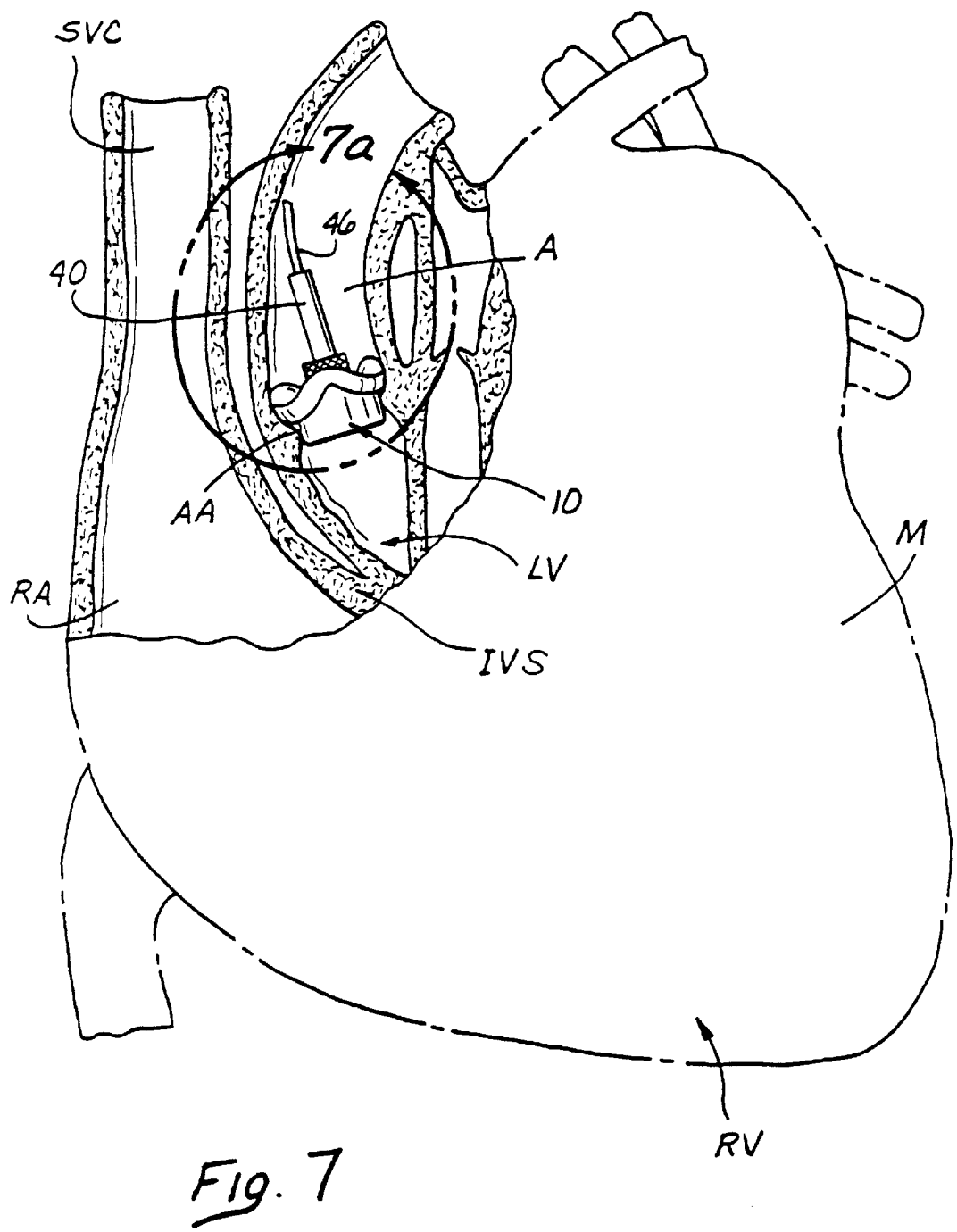
FIG. 7 is a perspective schematic view of a portion of a human heart, showing the manner in which the preferred aortic valve sizing obturator of the present invention is inserted into the surgically-prepared aortic annulus.

FIGS. 7–7a provide a schematic illustration of the typical manner in which the aortic valve sizing obturator 10 of the present invention may be utilized to determine the correct prosthetic valve size to be used for supra-annular implantation in a human heart. In the showing of the human heart provided in FIG. 7, the major anatomical structures are labeled accordingly to the following legend:

A=Aorta
AA=Aortic Annulus
M=Myocardium
IVS=Interventricular Septum
RV=Right Ventricle
RA=Right Atrium
LV=Left Ventricle
SVC=Superior Vena Cava As shown, a handle such as that shown in FIG. 6b is initially inserted and engaged into the upper end of the hollow bore 34 of the sizing obturator 10, and the threaded distal projection 42a of the handle is rotatably advanced such that its external threads will rotatably engage the internal threads 36 formed within the bore 34 of the obturator 10. In this manner, the handle of the type shown in FIG. 6b is firmly attached to the obturator 10, and extends in a longitudinally coaxial fashion from the upper end of the obturator 10, as shown.

The diseased or damaged aortic valve leaflets, and all associated structures deemed necessary, are surgically removed. The surgeon may also remove any calcium from the valve annulus, to ensure proper seating of the suture ring of the prosthetic valve.

After the aortic valve annulus has been surgically prepared, the aortic valve sizing obturator 10 of the present invention will be inserted such that the cylindrical obturator body 12 passes downwardly through the surgically-prepared valve annulus with little resistance. The obturator 10 is then rotatably reoriented and further advanced until the under-surface 22 of the non-planar, multi-curvate flange becomes nested or seated within the non-planar, multi-curvate anatomical structure of the natural aortic root. In this manner, the surgeon may visually verify that the diameter of the cylindrical obturator body 12 and non-planar, multi-curvate annular flange 18 are correct for that particular patient. Thereafter, the surgeon may select a prosthetic aortic valve which has a mounting (annulus) diameter and external sewing ring diameter the same as that of the obturator 10 which was found to correctly fit within the patient's aortic valve annulus. Thereafter, the obturator 10 and accompanying handle may be extracted and removed, and the selected prosthetic aortic valve may be sutured into place. Following use, the handle may be rotatably detached and removed from the obturator 10, and both the stainless steel handle and the molded plastic obturator may be autoclaved or otherwise sterilized for subsequent reuse.

It will be appreciated that the present invention has been described hereabove with reference to certain presently preferred embodiments only, and no effort has been made to exhaustively describe all possible embodiments in which the invention may take physical form. It will be appreciated by those skilled in the art that various addition, deletions, modifications and alterations may be made to the above-described embodiment without departing from the intended spirit and scope of the present invention. Accordingly, it is intended that all such additions, deletions, modifications and alterations be included within the scope of the following claims.

What is claimed is:

1. A reusable aortic valve sizing obturator apparatus comprising:
    a cylindrical obturator body having a central axis, a top end, a bottom end, and an outer surface;
    said cylindrical obturator body having a first outer diameter;
    a rigid annular flange member extending generally radially outward from said cylindrical obturator body, said flange member having an upper surface, an undersurface, and a second outer diameter, said second outer diameter being larger than said first outer diameter said cylindrical obturator body and said flange member being formed of materials suitable for sterilization in an autoclave; and,
    the undersurface of said flange member having, in a circumferential direction about said central axis, a non-planar, multi-curvate configuration.

2. The apparatus of claim 1 wherein the non-planar, multi-curvate configuration of the undersurface of said flange member comprises:

three circumferentially spaced-apart peaks with three arcuate depressions, each of said arcuate depressions extending between adjacent ones of said peaks.

3. The apparatus of claim 2 wherein said peaks are equidistantly spaced apart.

4. The apparatus of claim 1 wherein the entire annular flange member is of said non-linear, multi-curvate configuration.

5. The apparatus of claim 4 wherein the upper surface of said flange member is coterminous with the top end of said cylindrical obturator body, and wherein the top end of said cylindrical obturator body is also of said non-planar, multi-curvate configuration in said circumferential direction.

6. The apparatus of claim 1 wherein said obturator body further includes an inner surface and a cavity defined thereby, the apparatus further comprising:

an inner cylindrical member disposed longitudinally and coaxially within the cylindrical obturator body cavity, said inner cylindrical member being rigidly affixed to said obturator body inner surface and incorporating a handle connector apparatus whereby a separate handle member may be attached to said obturator apparatus.

7. The apparatus of claim 6 wherein said connector apparatus incorporated within said inner cylindrical member comprises:

a hollow bore extending longitudinally through at least a portion of said inner cylindrical member, and internal threads formed within said hollow bore such that an externally threaded handle may be rotatably engaged therewith.

8. The apparatus of claim 1 wherein the obturator body and flange member are monolithically formed.

9. The apparatus of claim 8, wherein the obturator body and flange member are formed of an autoclavable thermoplastic material.

10. A method for sizing an aortic valve annulus for subsequent placement therein of a prosthetic aortic valve, a superior aspect of the annulus having a natural aortic root shape, the method comprising the steps of:

a) providing a reusable aortic valve sizing obturator comprising:
  i) a cylindrical obturator body having a top end, a bottom end, an outer surface and a first outer diameter about a central axis;
  ii) a rigid flange member extending generally radially outward from said cylindrical obturator body, said flange member having an upper surface, an undersurface, and a second outer diameter, said second outer diameter being larger than said first outer diameter said cylindrical obturator body and said flange member being formed of materials suitable for sterilization in an autoclave;
  iii) the undersurface of said flange member having, in a circumferential direction about said central axis, a non-planar, multi-curvate configuration;
b) sizing said annulus by inserting said obturator into the aorta so that said cylindrical body fits within said aortic valve annulus and said flange member undersurface contacts the superior aspect of the aortic annulus; and
c) rotating said obturator about said central axis and further advancing said obturator so that said flange member undersurface conforms to the shape of the natural aortic root.

11. A method as claimed in claim 10 wherein the non-planar, multi-curvate configuration of the undersurface of said flange member comprises:

three spaced-apart peaks with three arcuate depressions, each of said arcuate depressions extending between adjacent ones of said peaks.

12. A method as claimed in claim 11 wherein said peaks are equidistantly spaced apart.

13. A method as claimed in claim 10 wherein the entire annular flange is of said non-linear, multi-curvate configuration.

14. A method as claimed in claim 13 wherein the upper surface of said flange member is coterminous with the top end of said cylindrical obturator body, and wherein the top end of said cylindrical obturator body is also of said non-planar, multi-curvate configuration.

15. A method as claimed in claim 10, wherein said obturator body further includes an inner surface and a cavity defined thereby, and wherein each valve sizing obturator additionally comprises:

an inner cylindrical member disposed longitudinally and coaxially within the cylindrical obturator body cavity, said inner cylindrical member being rigidly affixed to said obturator body inner surface and incorporating a handle connector apparatus whereby a separate handle member may be attached to said obturator apparatus.

16. A method as claimed in claim 15 wherein said connector apparatus incorporated within said inner cylindrical member comprises:

a hollow bore extending longitudinally through at least a portion of said inner cylindrical member, and internal threads formed within said hollow bore such that an externally threaded handle may be rotatably engaged therewith.

17. The method of claim 10, further including the steps of:

a) providing a plurality of said aortic valve sizing obturators having different diameter cylindrical obturator bodies;

b) selecting from the plurality of obturators one or more obturators as necessary whose cylindrical obturator body diameter approximates the diameter of the aortic valve annulus;

c) inserting, rotating, and advancing said one or more obturators within the annulus to conform the flange member to the shape of the natural aortic root; and, d) inspecting the relative fit of said one or more obturators in said annulus until a close fit is observed between both said obturator body and said annulus, and said flange member and the natural aortic root.

18. In a reusable aortic heart valve sizing obturator of the type comprising a generally cylindrical obturator body having a first diameter and a rigid annular flange which extends generally outward from said cylindrical obturator body, said flange having an undersurface which abuts against a superior aspect of the aortic annulus when said flange is positioned supra-annularly such that the cylindrical obturator body extends through the aortic annulus, said cylindrical obturator body and said flange being formed of materials suitable for sterilization in an autoclave, the improvement comprising:

a flange undersurface having, in a circumferential direction, a non-planar, multi-curvate configuration to conform to the shape of the superior aspect of the aortic annulus, thereby allowing said flange to nest against the superior aspect of the aortic annulus with the cylindrical obturator body extending through said annulus.

19. The improvement of claim 18 wherein said non-planar, multi-curvate configuration has three circumferentially spaced apart blunt peaks with arcuate depressions extending between said peaks.

20. The improvement of claim 19 wherein said blunt peaks and arcuate depressions are equidistantly sized and spaced-apart relative to each other.

21. A kit for determining the size of a prosthetic aortic heart valve to be implanted into a surgically-prepared aortic annulus within a mammalian heart, said kit comprising a plurality of reusable sizing obturators each having:

a generally cylindrical obturator body defining an outer surface having a first outer diameter; and, a rigid annular flange extending radially outward from said obturator body to a second outer diameter larger than said first outer diameter, said cylindrical obturator body and said flange being formed of materials suitable for sterilization in an autoclave, said flange having an upper surface and an undersurface with a circumferentially multi-curvate configuration, wherein at least the first diameter of one of said sizing obturators is different than the first diameter of another of said sizing obturators.

22. The kit of claim 21 wherein the multi-curvate configuration of the undersurface of each said sizing obturator flange comprises:

three circumferentially spaced-apart peaks with three arcuate depressions, each of said arcuate depressions extending between adjacent ones of said peaks.

23. The kit of claim 21 further including an elongate handle member alternately attachable to each of said sizing obturators, for inserting and subsequently removing selected ones of said obturators into said aortic annulus.

24. An aortic valve sizing obturator apparatus comprising:

a hollow, generally cylindrical obturator body defining an outer surface having a first outer diameter;

an annular flange extending radially outward from said obturator body to a second outer diameter larger than said first outer diameter, said flange having an upper surface and an undersurface with a circumferentially multi-curvate configuration having blunt peaks with arcuate depressions extending between said peaks; and a handle connector apparatus rigidly connected to said obturator body whereby a separate handle member may be attached to said obturator apparatus, said handle connector apparatus comprising a threaded member longitudinally oriented within the hollow cylindrical obturator body for rotatably coupling with a handle member, the threaded member being rigidly affixed to the cylindrical obturator body with radial strut members at locations corresponding to the blunt peaks on the flange member.

25. The apparatus of claim 24, wherein the multi-curvate configuration of the undersurface of said flange comprises:

three spaced-apart peaks with three arcuate depressions, each of said arcuate depressions extending between adjacent ones of said peaks.

26. The apparatus of claim 25, wherein said peaks are equidistantly spaced apart.

27. The apparatus of claim 24, wherein the entire annular flange is of said multi-curvate configuration.

28. The apparatus of claim 24, wherein the upper surface of said flange is coterminous with the upper end of said cylindrical obturator body, and wherein the upper end of said cylindrical obturator body is also of said multi-curvate configuration.

29. The apparatus of claim 24, wherein the cylindrical obturator body has an inner cylindrical surface, said thread member further comprising:

an inner cylindrical member disposed coaxially within the hollow cylindrical obturator body.

30. The apparatus of claim 29, wherein said connector apparatus incorporated within said inner cylindrical member comprises:

a hollow bore extending longitudinally through at least a portion of said inner cylindrical member, and internal threads formed within said hollow bore such that an externally threaded handle may be rotatably engaged therewith.

31. The apparatus of claim 24, wherein the multi-curvate configuration of the undersurface of said flange comprises:

three spaced-apart peaks with three arcuate depressions, each of said arcuate depressions extending between adjacent ones of said peaks, and wherein there are three of said radial strut members attached to an inner surface of the hollow cylindrical obturator body at locations adjacent each of the spaced-apart peaks formed in the multi-curvate flange.

* * * * *